United States Patent [19]

Bodart et al.

[11] 4,395,494

[45] Jul. 26, 1983

[54] REAGENT AND METHOD FOR THE DETERMINATION OF HYDRAZINE

[75] Inventors: Detlef Bodart, Darmstadt; Roland Bitsch, Pfungstadt, both of Fed. Rep. of Germany

[73] Assignee: Merck Patent Gesellschaft mit Beschränkter Haftung, Darmstadt, Fed. Rep. of Germany

[21] Appl. No.: 200,249

[22] Filed: Oct. 24, 1980

[30] Foreign Application Priority Data

Oct. 24, 1979 [DE] Fed. Rep. of Germany ....... 2942960

[51] Int. Cl.$^3$ ............................................. G01N 33/00
[52] U.S. Cl. .................................................... 436/111
[58] Field of Search ........................ 252/408; 424/232; 23/230 R; 436/111

[56] References Cited

U.S. PATENT DOCUMENTS 3,424,845  1/1969  Berndt et al. ........................ 424/232
3,549,329  12/1970 Silverman et al. ................... 436/111
3,621,095  11/1971 Berndt et al. ........................ 424/232
4,200,608  4/1980  Croomes et al. .................... 436/111

OTHER PUBLICATIONS

*Chemical Abstracts*, vol. 83, (1975), abstract 175162v, Matsutani, M.
*Chemical Abstracts*, vol. 83, (1975), abstract 130105n, Dixon, E. J. et al.
G. A. Ellard et al., Biochemical Journal, vol. 126, pp. 449-458, (1972).
J. H. Peters et al., Analytical Biochemistry, vol. 12, p. 379, (1965).

*Primary Examiner*—T. S. Gron
*Assistant Examiner*—M. Moskowitz
*Attorney, Agent, or Firm*—Millen & White

[57] ABSTRACT

4-dimethylaminocinnamaldehyde can be used as a reagent for determination of hydrazine in an aqueous solution. The reagent is especially stable and useful when dissolved in an ethylene glycol monoalkyl ether.

9 Claims, No Drawings

REAGENT AND METHOD FOR THE DETERMINATION OF HYDRAZINE

BACKGROUND OF THE INVENTION

The present invention relates to a stable reagent and a method for the determination of hydrazine in aqueous solutions.

Hydrazine is a known anti-corrosive agent for steel in contact with water, for example, in steam boiler operation, in warm water circulation systems and in the shut-down preservation of vessels and the like. Depending on the temperature and pressure conditions, 0.1–300 ppm of hydrazine are added to the water. Systems under higher pressures and at higher temperatures require the smallest amounts of hydrazine. As a result of the consumption of hydrazine during operation of the steam boiler, the hydrazine contents susceptible to measurement frequently fall below 0.1 ppm. Hitherto, it has not been possible to measure these low concentrations with simple rapid tests. However, in boiler operation, the residual hydrazine content in the range below 0.1 ppm is an important parameter. This determines the time at which further hydrazine is metered in and the amount of the additionally metered hydrazine.

There is a standard method for the determination of hydrazine in water. Since its introduction in 1947, this method has formed the basis of all factory laboratory methods and rapid test methods. The reaction involved is that of hydrazine with 4-dimethylaminobenzaldehyde to produce 4-dimethyl aminobenzaldehyde azine (Bull. Soc. Chim. France, 122–123 (1947)). On the other hand, it is also known that primary and secondary aromatic amines in methanol in the presence of trichloroacetic acid give a more sensitive and deeper coloration with 4-dimethylaminocinnamaldehyde than with B 4-dimethylaminobenzaldehyde (Chemical Abstracts 55, 19616b (1960)).

However, the established and reliable method of determination of hydrazine using 4-dimethylaminobenzaldehyde has the decisive disadvantage that the solution of the 4-dimethylaminobenzaldehyde is yellow while the corresponding azine which is formed likewise has a yellow color, although this is somewhat deeper. Since the eye is able to differentiate differences in yellow intensities less well than differences in the intensities of other colors, only relatively rough grading of the hydrazine concentrations, e.g., of 0–0.1–0.25–0.5–1.0 ppm of hydrazine, has been possible hitherto with the optical test. Particular difficulties arise in the case of low hydrazine contents. These are especially difficult to assign by gradings of pale yellow shades since the blank is already yellow in color. A further problem is the optical measurement in artificial light, under which the differentiability of yellow shades is in general even poorer.

On the other hand, in contrast to 4-dimethylaminobenzaldehyde, 4-dimethylaminocinnamaldehyde has poor stability in solution. However, it is absolutely essential that a liquid ready-for-use reagent have good stability so that it will not be necessary to prepare a fresh reagent solution before each determination.

SUMMARY OF THE INVENTION

Accordingly, it is an object of this invention to provide a stable, sensitive reagent and a method for the determination of hydrazine in aqueous solutions, with which extremely small hydrazine contents can still be reliably detected.

Upon further study of the specification and appended claims, further objects and advantages of this invention will become apparent to those skilled in the art.

These objects have been attained by providing, in one aspect, an agent for the determination of hydrazine in aqueous solutions, which contains 4-dimethylaminocinnamaldehyde. Preferably, the agent is in the form of a 2 to 4 wt.%, and in particular about a 3 wt.% solution of 4-dimethylaminocinnamaldehyde in an ethylene glycol monoalkyl ether, in particular ethylene glycol monoethyl ether. The alkyl portion generally has 1–4 C atoms.

The present invention also relates in another aspect to a method for the determination of hydrazine in aqueous solutions, which comprises adding a solution of 4-dimethylaminocinnamaldehyde in an ethylene glycol monoalkyl ether to the hydrazine-containing sample solution and determining the content of the 4-dimethylaminocinnamaldehyde azine formed by colorimetry.

DETAILED DISCUSSION

Surprisingly, it has been found that a solution of 4-dimethylaminocinnamaldehyde in an ethylene glycol monoalkyl ether has very good stability and that accurate and reproducible analytical results are obtained using this solution in hydrazine determinations, even in the range below 0.1 ppm of hydrazine.

The increase in reaction contrast using the agent of this invention results in a color series from yellow via orange to wine-red. A ten-step grading is possible which can be measured optically equally well either in daylight or under artificial light. In the case of photometric measurements also, the high reaction contrast ($\Delta\lambda$) of 135 nm, compared with that of only 45 nm in the case of the conventional method using 4-dimethylaminobenzaldehyde, is advantageous. Since the extinction maximum of 540 nm, is in the red region and is scarcely influenced by yellowish intrinsic colors of water, the conventional color compensation samples, which were previously necessary in these cases and in which the hydrazine had to be eliminated in an additional batch operation can be eliminated.

The determination of hydrazine per this invention can be readily carried out by acidifying the sample solution (e.g., to a pH of about 0.8) and adding the solution of 4-dimethylaminocinnamaldehyde in an ethylene glycol monoalkyl ether. Acids which can be used for the acidifying operation include all acids which do not interfere with the determination, preferably mineral acids, such as sulfuric acid, hydrochloric acid, perchloric acid, phosphoric acid and the like. Mixtures of sulfuric acid with perchloric acid have proved particularly suitable. Generally, 1–5 vol.% of the reagent solution of the invention, based on the volume of test solution, is added.

After the sample solution and reagent solution have been mixed well, visual or spectrophotometric evaluation is carried out after 5 to 20 minutes. If the determination is carried out in a round-bottomed glass tube, visual evaluation is carried out with the aid of a color scale. The latter is routine and conventionally constructed by carrying out the method of this invention on hydrazine samples of known concentration. Every 0.01 ppm of hydrazine can be reliably detected by this method. If the determination is carried out in a cell, the spectrophotometric measurement is carried out at 540 nm, again using a predetermined calibration curve according to conventional practice.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

0.2 ml of a sulfuric acid/perchloric acid mixture (7 parts of 25% sulfuric acid and 3 parts of 70% perchloric acid) and 0.15 ml of a 3% solution of 4-dimethylaminocinnamaldehyde in ethylene glycol monoethyl ether are added to 5 ml of a solution, which can contain between 0.2 and 4 ppm of hydrazine, in a round-bottomed glass tube with a diameter of 24 mm. After thorough mixing and standing for about 10 minutes, the glass tube is fixed above a white base. When observed from above, a distinct color gradation from yellow to red is discernible and this can be unequivocally assigned to the hydrazine contents with the aid of a predetermined standard color scale.

EXAMPLE 2

0.4 ml of a sulfuric acid/perchloric acid mixture (7 parts of 25% sulfuric acid and 3 parts of 70% perchloric acid) and 0.3 ml of a 3% solution of 4-dimethylaminocinnamaldehyde in ethylene glycol monoethyl ether are added to 20 ml of a solution which can contain between 0.02 and 0.25 ppm of hydrazine. When observed from above in a flat-bottomed glass tube which has a diameter of 20 mm and has been placed on a white base, this gives a distinct color gradation from yellow to orange-red. The hydrazine contents can be determined exactly with the aid of a color scale as in Example 1.

EXAMPLE 3

0.2 ml of a sulfuric acid/perchloric acid mixture and 0.15 ml of a 3% solution of 4-dimethylaminocinnamaldehyde in ethylene glycol monoethyl ether are added to 5 ml of a solution which can contain between 0.05 and 4.5 ppm of hydrazine. After standing for 10 minutes, the coloration is measured in a cell with a layer thickness of 10 mm, at 540 nm in a spectrophotometer against a blank prepared at the same time. Using the extinction value measured, the concentration of hydrazine is read off from a calibration curve plotted beforehand with hydrazine solutions for which the contents were accurately known.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A reagent for use in the colorimetric determination of hydrazine in an aqueous solution comprising 4-dimethylaminocinnamaldehyde and an ethylene glycol mono-$C_{1-4}$-alkylether.

2. A reagent of claim 1 comprising 2 to 4 wt.% of 4-dimethylaminocinnamaldehyde.

3. A reagent of claim 1 wherein the ethylene glycol monoalkyl ether is ethylene glycol monoethyl ether.

4. A reagent of claim 1 wherein the reagent consists essentially of a solution of the 4-dimethylaminocinnamaldehyde in the ethylene glycol mono-$C_{1-4}$-alkylether.

5. A reagent as in claim 4 wherein the ethylene glycol monoalkyl ether is ethylene glycol monoethyl ether.

6. A reagent as in claim 4 comprising 2 to 4 wt.% of 4-dimethylaminocinnamaldehyde.

7. A reagent of claim 2 wherein the amount of 4-dimethylaminocinnamaldehyde is about 3 wt.%.

8. A reagent of claim 6 wherein the amount of 4-dimethylaminocinnamaldehyde is about 3 wt.%.

9. A reagent of claim 2 wherein the ethylene glycol monoalkyl ether is ethylene glycol monoethyl ether.

* * * * *